Figure 1:
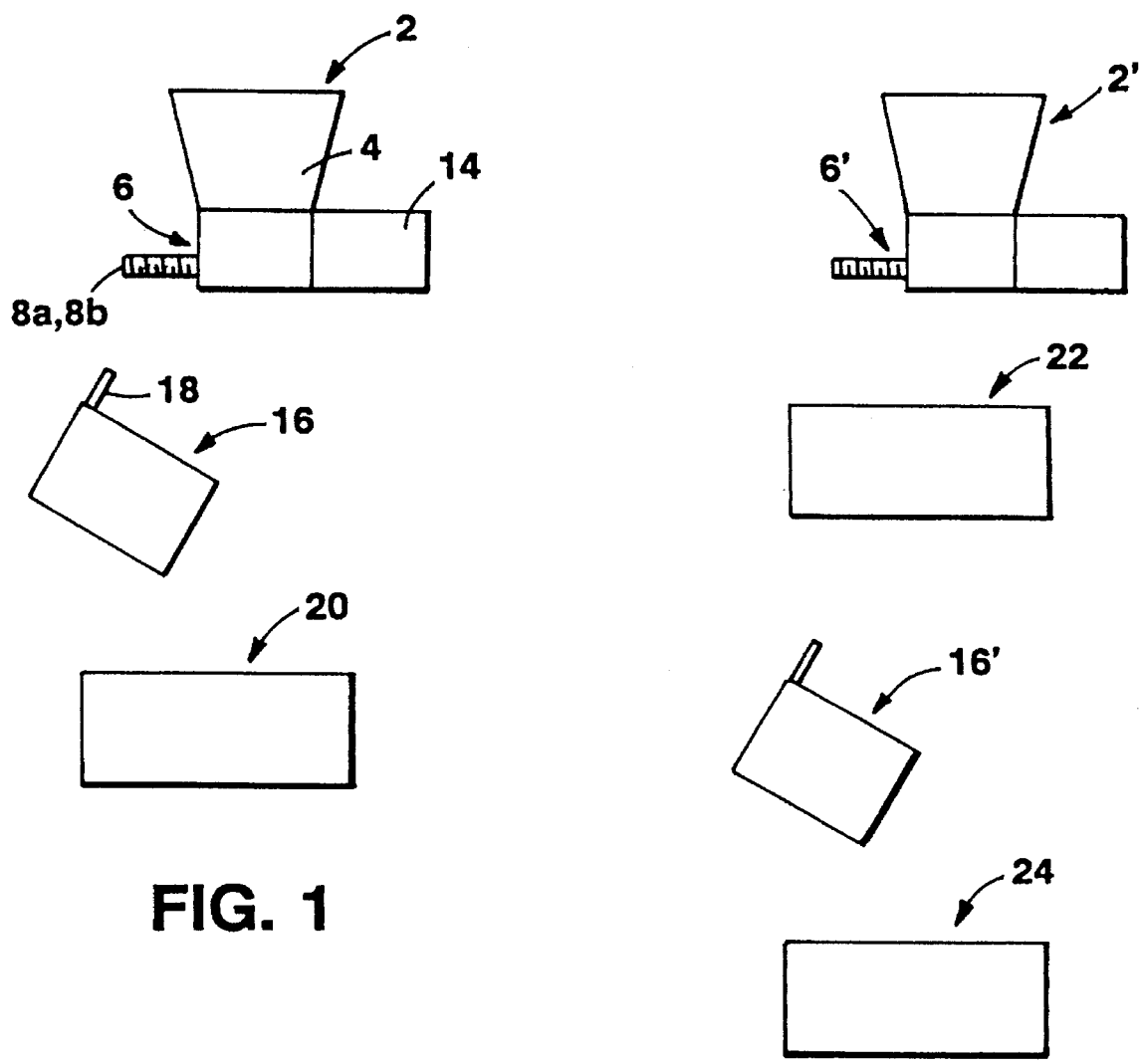

United States Patent [19]
Trofast et al.

[11] Patent Number: 5,551,489
[45] Date of Patent: Sep. 3, 1996

[54] AGGLOMERATION OF FINELY DIVIDED POWDERS

[75] Inventors: Eva A. C. Trofast; Erik J. Falk, both of Lund, Sweden

[73] Assignee: Astra Aktiebolag, Sodertalje, Sweden

[21] Appl. No.: 317,033

[22] Filed: Oct. 3, 1994

[51] Int. Cl.$^6$ .............................. B65B 1/04; B65B 3/04
[52] U.S. Cl. ............................ 141/18; 141/69; 241/76; 241/153; 209/2; 209/3; 366/221
[58] Field of Search ................................. 141/1, 69, 18, 141/34, 98, 286; 222/238; 241/284, 24, 29, 76, 77, 78, 153; 209/2, 3, 10; 264/15, 117; 366/220, 221, 225

[56] References Cited

U.S. PATENT DOCUMENTS

| | | | |
|---|---|---|---|
| 2,609,150 | 9/1952 | Bludeau | 241/76 |
| 3,043,480 | 7/1962 | Wittrock | 222/238 |
| 3,802,822 | 4/1974 | Harbison | 366/221 |
| 4,688,610 | 8/1987 | Campbell | 141/83 |
| 4,826,325 | 5/1989 | Iwata et al. | 366/221 |
| 4,940,556 | 7/1990 | MacFarlane et al. | 264/15 |
| 5,143,126 | 9/1992 | Boesch et al. | 141/1 |
| 5,394,868 | 3/1995 | Ambrosio et al. | 128/203.15 |

FOREIGN PATENT DOCUMENTS

| | | |
|---|---|---|
| 0072046 | 2/1983 | European Pat. Off. . |
| 0241126 | 10/1987 | European Pat. Off. . |
| 0291201 | 11/1988 | European Pat. Off. . |
| 0490649 | 6/1992 | European Pat. Off. . |
| 1242211 | 8/1971 | United Kingdom . |
| 1520247 | 8/1975 | United Kingdom . |
| 1569611 | 6/1980 | United Kingdom . |
| 2187952 | 9/1987 | United Kingdom . |

OTHER PUBLICATIONS

Kugler, "Vibrating Screens for Aggregate Production"*Bulk Solids Handling*, vol. 6, No. 2, pp. 397–400 (Apr. 1986).
Pietsch, "Size Enlargement by Agglomeration", *John Wiley & Sons*, (1991).
Iinoya et al., "Powder Technology Handbook" (1991).
Staffa et al., "Flowability of Powders under the Influence of Vibrations", *Powder Metallurgy International*, vol. 9, No. 1 (1977).
Pilpel, "Cohesive Pharmaceutical Powders", *Adv. Ph. Sc.*, vol. 3, pp. 173–219 (1971).
Neumann, "The Flow Properties of Powders", *Advances in Pharm. Sci.*, vol. 2 (1967).
Claussen et al., "Kugelherstellung durch Pulveragglomeration", *J. of Materials Technology*, vol. 4, pp. 148–156, (1973).
Hicks et al., "Extrusion and Spheronizing Equipment", *Pharmaceutical Pellitization Technology*, pp. 86–98 no date available.

*Primary Examiner*—Henry J. Recla
*Assistant Examiner*—Steven O. Douglas
*Attorney, Agent, or Firm*—Fish & Richardson P.C.

[57] ABSTRACT

A method and system for improving the flow properties of finely divided powders is provided. The method includes (a) agglomerating the powder by passing it through a screw feeder; and (b) spheronizing the agglomerates. The method preferably further includes (c) sizing the spheronized agglomerates. Spheronization is preferably accomplished by tumbling the agglomerates in a tilted rotating container.

26 Claims, 3 Drawing Sheets

| SIZE FRACTION | METERED DOSE (mg/dose) |
|---|---|
| <0.14 | 0.65 |
| 0.14-0.3 | 0.62 |
| 0.3-0.5 | 0.59 |
| >0.5 | 0.55 |

AGGLOMERATION OF FINELY DIVIDED POWDERS

BACKGROUND OF THE INVENTION

The present invention relates to methods and devices for the agglomeration of finely divided powders, e.g., powdered medicaments for inhalation therapy.

Finely divided powders, i.e., powders having a very small particle size, typically less than 5–10 μm, are commonly used in inhalation therapy. In this application, the particle size of the powder is of the utmost importance. The diameter of the particles to be inhaled must be less than 10 μm or the particles will not adequately penetrate the bronchial area of the lungs. It is also very important in inhalation therapy that a precisely controlled dosage be administered. The inhaled route of administration enables the dose to be delivered directly to the airways, and thus allows a very small dosage to be given, minimizing side effects, but also making precise metering of the powder dosage crucial.

Particle size control and precise metering are often made problematic by the flow properties of finely divided powders. Most finely divided powders are light, dusty and fluffy. Further, the van der Waals forces of the particles exceed the force of gravity, causing the particles to be cohesive. This combination of properties makes the powder flow poorly, complicating handling, processing and storage, and making it difficult to meter and dispense a precise dosage of the powder. The particles also tend to adhere to each other during storage and handling, forming agglomerates. Because these agglomerates are made up of a number of primary particles, they typically have diameters in excess of 10 μm. Accordingly, if the agglomerates do not break down into primary particles during inhalation the powder dosage will not properly penetrate the bronchial area. Also, if agglomeration is not controlled, random sized agglomerates may result, making precise metering of the powder difficult.

The flow properties of the powder can be improved by controlled agglomeration of the powder, e.g., by vibration, agitation or rolling of the powder with or without a binder. However, the agglomerates must have sufficiently low internal coherence so that they readily break into primary particles during inhalation in an inhalation device.

Methods of controlled agglomeration are known in the art. For example, Claussen and Petrow (Journal of Materials Technology, vol 4(3), pp. 148–156 (1973)) describe a method of agglomeration by tumbling in a cylinder tilted at an angle to the horizontal axis of rotation. U.S. Pat. No. 5,143,126 describes a vibratory conveyor for forming flowable agglomerates from previously poorly flowable fine-grained powder by subjecting the powder to a mechanical vibration step prior to transport and metering. GB 1,569,611 describes a process for agglomeration of a drug into soft pellets, using a binder to produce a paste which is extruded through a sieve to create agglomerates. GB 2,187,952 describes a method of agglomeration by kneading a crystalline powder as it is conveyed by conveying screws through an extruder.

SUMMARY OF THE INVENTION

The invention features a method of treating a finely divided powder that includes feeding the powder through a screw feeder to form agglomerates, and spheronizing the agglomerates. This process has been found to produce agglomerates having excellent handling properties, which have sufficient strength to withstand packaging and storage, but which are sufficiently soft so that they will easily break down into primary particles when they are expelled from an inhaler during inhalation therapy. In preferred embodiments, the agglomerates have a hardness of less than 100 mN, more preferably less than 20 mN, and most preferably between 0.5 and 20 mN as measured by a MHT-4 Microhardness tester (A. Paar, Austria).

The method is particularly suitable for use with finely divided powdered medicaments having a particle size of less than about 10 μm. In preferred aspects, the medicament is selected from the group consisting of terbutaline, budesonide and lactose. Typically, the agglomerates after the final step of the method have a diameter of less than about 2 mm, a bulk density of from about 0.2 to 0.4 g/ml, and a surface area of from about 2–20 $m^2/g$.

Preferably, the screw feeder comprises twin concave screws, preferably having a pitch of from about 2 to 20 mm.

In preferred aspects, the spheronization step comprises placing the agglomerates in a tilted container and rotating the container to tumble the agglomerates. Preferably, the container is a granulating pan, is provided with at least one scraper, and is tilted at an angle of from 10°–80° from the vertical. More preferably, the container is tilted at an angle of from 30°–60° from the vertical. Preferably, the spheronization step is performed for about 2 to 20 minutes and the container is rotated at a periphery speed of from about 0.5 to 1.0 m/s.

Preferably, the method further includes sizing the agglomerates by passing the agglomerates through a sieve. This sizing may take place after agglomeration, after spheronization, or both. Where the agglomerates are sized after spheronization, a subsequent spheronization step may be performed after this sizing step.

In another aspect, the method further includes metering a predetermined amount of the spheronized agglomerates into a breath actuated dry powder inhaler provided with means for deagglomerating the agglomerates during inhalation. In this aspect, the method may further include the step of actuating the inhaler, causing the agglomerates to be deagglomerated into primary particles by the means for deagglomerating.

BRIEF DESCRIPTION OF THE DRAWINGS

FIG. 1 shows a schematic view of a first embodiment of an apparatus according to the invention.

FIG. 2 shows a schematic view of the screws in the screw feeder.

FIG. 3 shows a schematic view of a second embodiment of an apparatus according to the invention, FIG. 4 is a diagram showing a comparison of the size of the agglomerated particles as a function of different screws.

FIG. 5 is a diagram showing size distribution of spheres as a function of different screws.

FIG. 6 is a diagram of a sieving analysis of micronised terbutaline sulphate processed in an apparatus according to the invention.

FIG. 7 is a diagram showing the relationship between different fractions of the substance and the metered dose.

DESCRIPTION OF THE PREFERRED EMBODIMENTS

A powder treatment system 1 is shown schematically in FIG. 1. The system includes an agglomerator 2 including a container 4 and a screw feeder 6 in fluid communication with the container 4. The screw feeder 6 includes at least two cooperating screws 8a, 8b disposed within a snugly fitting housing 9. A finely divided powder, e.g., a powdered medicament, is supplied to the screw feeder device 6 through the container 4. The container 4 is provided with a mechanical stirring device (not shown) to facilitate the feeding of the cohesive powder to the screws. One suitable stirring device includes a plurality of L-shaped elongated members mounted to rotate about an axis of rotation which is substantially parallel to the longitudinal axis of the screws in a manner so that powder is lifted and scraped from the sides of the container and urged towards the screws. Any type of mechanical stirring device that will facilitate powder feeding may be used. Suitable screw feeders include the K-TRON SODER standard twin-shaft feeder without agitator and the Brabender twin-screw feeder type DDSR/20.

As the powder passes through the screw feeder device 6 it passes between the screws 8a, 8b. Pressure is exerted on the powder particles by the twisting movement of the screws 8a, 8b, driven by a motor 14. The pressure exerted by the screws as they force the powder forward causes the powder particles to be pressed together and to form soft agglomerates of different sizes. The agglomerated particles which are thus produced typically have a size between 0.1 mm –2 mm, are flowable, due to their size, and are comparatively soft in their structure.

Figure 2:
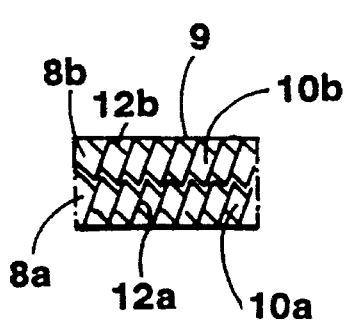

Preferably the screws are what is referred to as "twin-concave screws", as shown in FIG. 2. The screws have substantially identical pitch, and are positioned so that the threads of each screw fit in the flights (valleys) between the threads of the other. Twin-concave screws having a short pitch (distance between threads) will generally give the most uniform agglomerates having the best properties for meeting the requirements for powders for inhalation. In a preferred embodiment of the invention the pitches of the screws are between 2–20 mm, preferably between 5–15 mm.

During operation of the screw feeder, the powder is mechanically forced into the flights (valleys) 10a, 10b between the threads 12a, 12b of the cooperating screws 8a, 8b as the screws rotate. As the screws rotate, the thread 12a of one screw 8a will move into the flight 10b of the other screw 8b, thereby removing adhered powder from the opposed screw and forcing the powder forward at the same time. The screws typically rotate in the same direction (counter rotation would cause one screw to travel with respect to the other) and at the same speed.

The length and the rotation speed of the screws usually have little effect on agglomerate properties, while the pitch of the screws and the distance between the threads are of importance. More dense and uniform agglomerates are obtained when the threads of one screw are as close to the threads of the cooperating screw as possible. The difference between the diameter of the screw at the highest point of the thread and the diameter at the lowest point of the flight, i.e., the thread height, is preferably between 1 –10 mm, more preferably between 1–5 mm. If this distance is too big the agglomerates will not have the well defined dimensions which are required. In a preferred embodiment the diameter of the screw at the peak of the thread is 20 mm and the diameter at the bottom of the flight is between 10–19 mm, preferably between 15–19 mm.

It is also important, in order to obtain the desired agglomerate properties, that the housing 9 around the screws in the screw feeder fits around the screws in a tight manner leaving only enough space between the walls of the housing and the screws to allow the screws to rotate. If there is a distance between the wall and the screws, finely divided powdered medicament will be compacted in this area during the rotation of the screws and the agglomeration procedure will result in a less uniform product. Preferably the gap is less than 1 mm.

After the agglomeration procedure, the agglomerates can be transported to a sieving device in order to obtain agglomerates within a certain range of size if desired.

The agglomerates obtained from the screw feeder have different sizes and are comparatively soft, and thus need to be further treated to obtain the desired characteristics. The agglomerates are therefore collected in a rotating pan or drum 16 which is preferably provided with one or more scrapers 18 (only shown schematically in the drawings), and which is tilted. Preferably the scraper is mounted so that it will contact and scrape down the inner wall of the pan as the pan is rotated, to prevent powder from sticking to the wall. The pan may be metal, plastic, or any other suitable material, so long as it is inert and does not contaminate the powder. It may be desirable to ground the pan to prevent build-up of electrostatic charges. A preferred type of pan is a "granulating pan", a type of granulating device that is well known in the art. The tilting angle of the pan or drum 16 is preferably between 10°–80° from the vertical, more preferably between 30°–60°. The rotation of the tilted pan or drum 16 will make the agglomerates roll and tumble, causing the agglomerates to be "spheronized". The scraper increases the rolling and tumbling of the agglomerates, thereby improving spheronization.

This spheronization gives the agglomerates a stronger, more spherical, dense, compact and uniform form and a smoother outer surface. These characteristics will further improve the flowability and the resistance of the agglomerates to breaking during handling and storage. The rotational velocity of the pan or drum determines the characteristics of the agglomerates after spheronization. Preferably, the periphery speed (the rotational velocity of the pan or drum measured at a point its the periphery) of the pan or drum is between 0.2–2.0, more preferably between 0.5–1.0 m/s. The preferred spheronization time is preferably between 2–20 min. After 20 minutes, the agglomerates typically have reached an optimal size, capability of breaking down and density. The longer the agglomerates are spheronized, the harder and larger the agglomerates will become.

After spheronization, the agglomerates are passed through a sieve 20 having an aperture size between 0.2–2.0 mm, preferably between 0.3–1.0 mm, in order to obtain a uniform size of the agglomerates. This sieving step is typically necessary as a final processing step, to ensure uniformity. However, there may be some instances in which, due to the nature of the inhaler in which the agglomerates are to be used, sieving will not be necessary.

To minimize the number of agglomerates which are too big and therefore have to be discarded or undergo the entire agglomeration process again before they can be used, it is preferred to incorporate further steps of sieving and spheronization into the process. In a particularly preferred process, a further sieving step is incorporated into the process directly after the agglomeration process in the screw feeder. After this sieving the agglomerates are spheronized in the granulating pan or drum and a second further sieving step is carried out after this spheronization. A second spheronization step is then carried out and the whole process is ended by the final sieving step. These further steps of sieving and spheronization will provide a more effective process and the agglomerates obtained after the second spheronization are uniform and have particularly desirable characteristics. An apparatus according to this embodiment of the invention is shown in FIG. 3.

Figure 3:
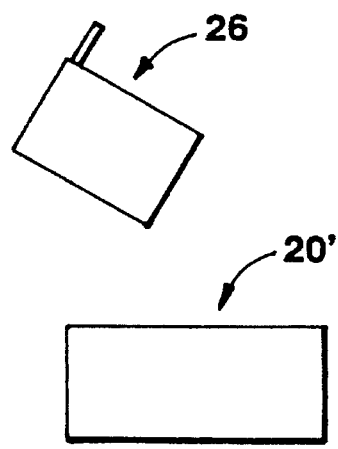
Figure 4:
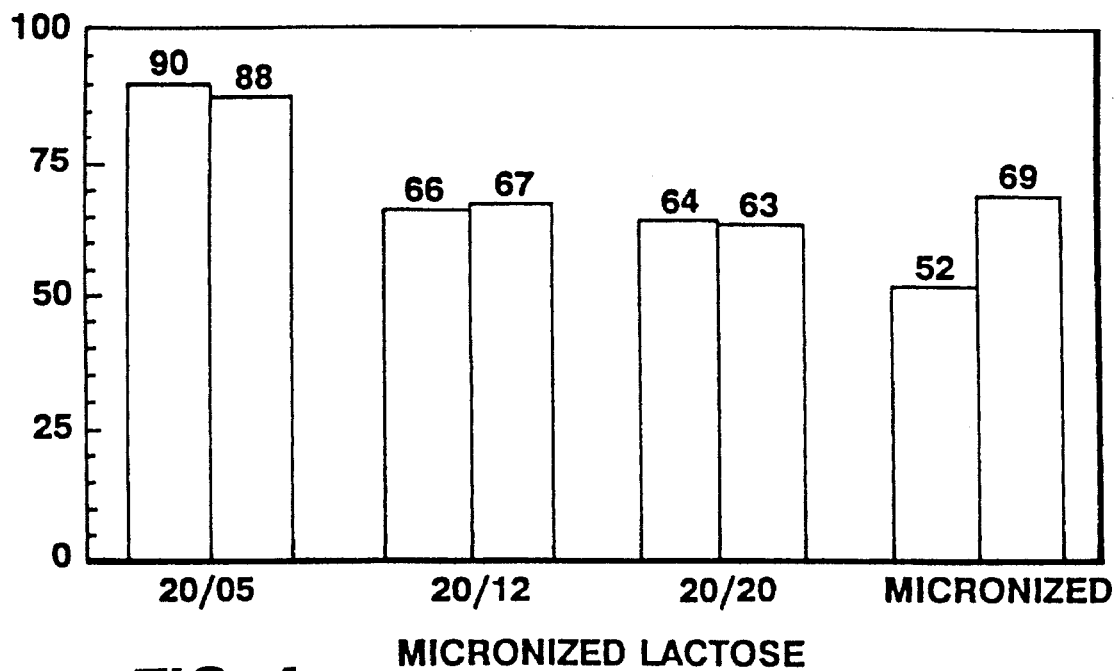
Figure 5:
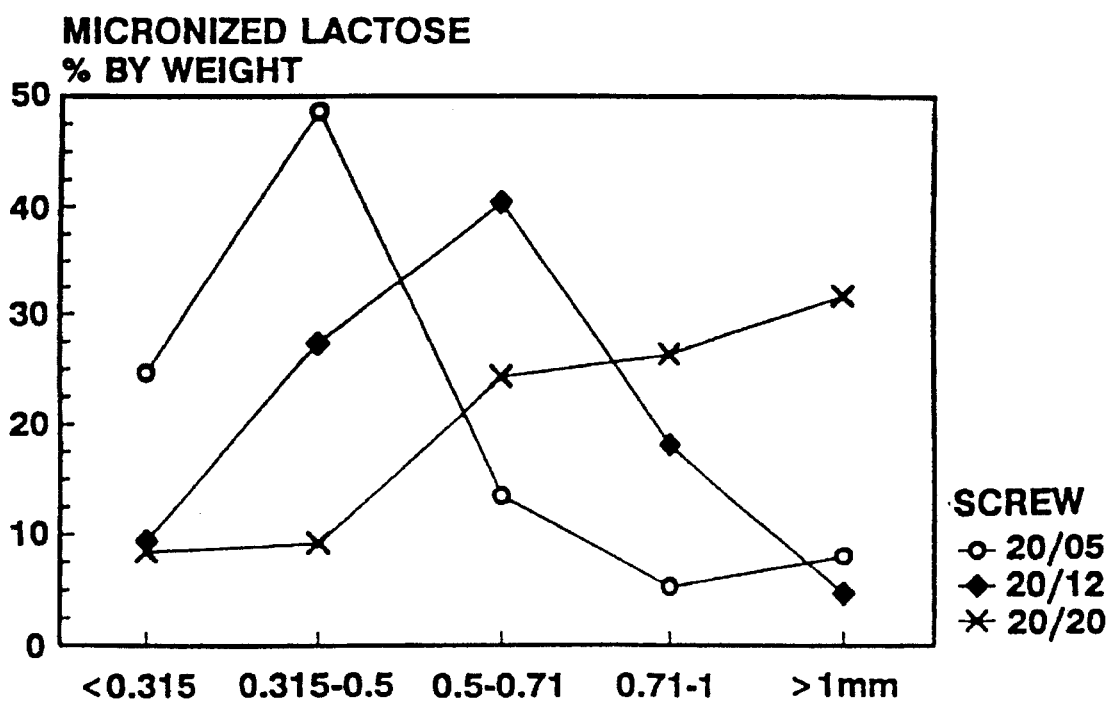
Figures 6, 7:
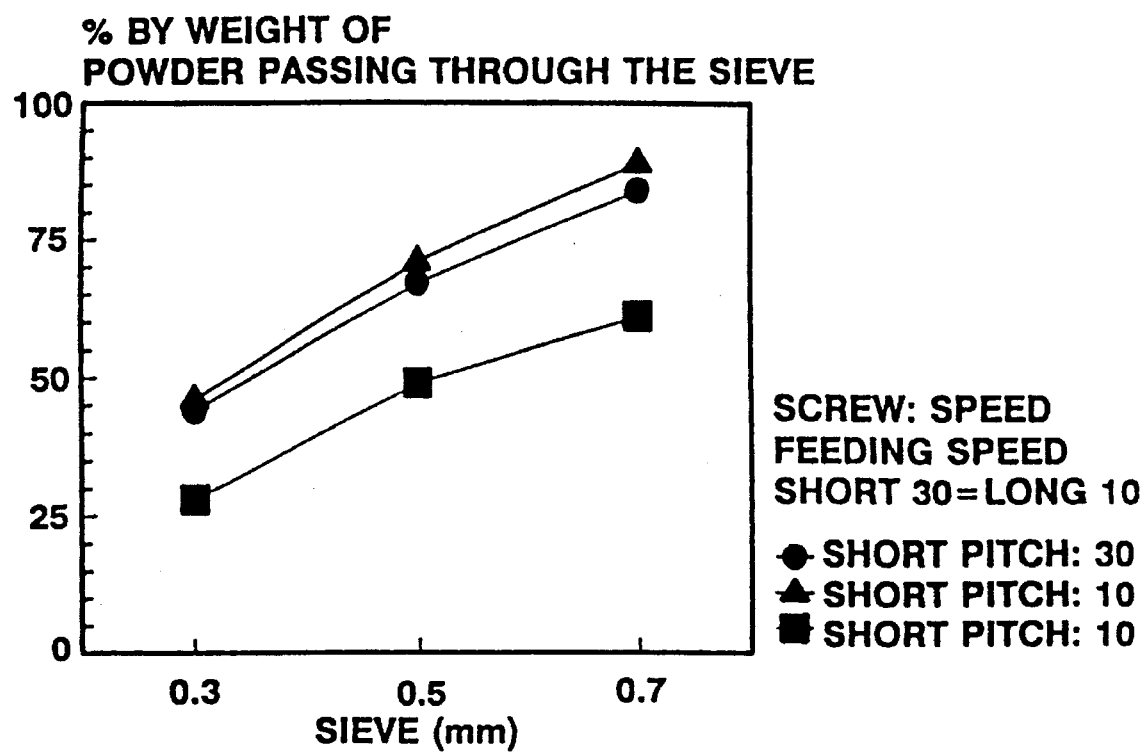

As shown in FIG. 3, the finely divided powdered medicament is agglomerated in the screw feeder device 6' and the resulting agglomerates are supplied to a sieve 22. The sifted agglomerates are thereafter supplied to the tilted granulating pan or drum 16'. After spheronization in the pan or drum 16' the agglomerates are supplied to a second sieve 24 to obtain a more uniform size. Next, the agglomerates are spheronized a second time in a second tilted granulating pan or drum 26. This second granulating pan or drum 26 is of the same type as the first pan or drum and the preferred periphery speed and the spheronization time are the same as for the first step of spheronization. After this second spheronization the agglomerates are sifted through a final sieve 20' to obtain a uniform particle size. This final sifting step is necessary in some cases, if the agglomerates become larger during spheronization than the required particle size, e.g., the particle size distribution exceeds 0.2–2 mm. Preferably the final sifting step is performed if the particle size distribution exceeds 0.3–1 mm.

At the end of processing, it is preferred that the spheronized agglomerates have a hardness of less than 100 mN, more preferably less than 20 mN, and most preferably between 0.5 and 20 mN as measured by a MHT-4 Microhardness tester (A. Paar, Austria). Agglomerates having a hardness of greater than 100 mN may not disintegrate properly during inhalation, while agglomerates having a hardness of less than 0.5 mN may not have sufficient hardness to withstand processing and packaging.

The agglomeration process according to the invention will be illustrated by the following examples.

Example 1

Micronised terbutaline sulphate with a mass medium diameter (MMD) of 1.2 μm was added to a K-tron Soder twin-shaft feeder (speed 15 gram/min) using long-pitch twin concave screws.

In order to observe the formation of the agglomerates obtained from the method of the invention the end plate of the screw feeder was removed and a high-speed video camera was installed at the end of the screws. It was then possible to visualize the resulting product from the screw feeder and compare the formed agglomerates with non-treated powder under different experimental conditions. Samples were taken and were further examined under a microscope. Irregular and soft agglomerates were obtained.

In a further experiment, the long-pitch screws were changed to short-pitch twin concave-profile screws of the same type and the same substance was added to the same equipment and under the same experimental conditions. The resulting agglomerates were more regular than those obtained from the long pitch screws.

Example 2

Micronised lactose (MMD<4 μm) was added to a Brabender twin-screw feeder type DDSR/20 with different twin-screw sizes (diameter/pitch=20/11, 20/12, 20/20). The soft agglomerates from the feeder were added to a gyro-vibrating sieve with a mesh size of 0.5 mm. The velocity of feeding on the sieve was adjusted so that the powder passed the sieve at once, i.e. no agglomeration occurred on the sieve. Two experiments for each screw were performed. The data obtained indicated that larger screws (e.g. 20/20) result in less defined and larger agglomerates.

As a comparative experiment, micronised powder was slowly added by a spoon directly on the sieve, i.e. without passing the screw feeder. Great variation of the size of the agglomerates was obtained, which indicates the necessity of using a screw feeder to obtain uniform agglomerates (essential to accurate dosage in an inhaler device) and a satisfactory yield.

A summary of these experiments is shown in FIG. 4.

Example 3

Agglomerates of micronized lactose obtained from a Brabender twin-screw feeder type DDSR/20 were rotated at 35 rpm in a pan (diameter 320 mm) for 5 min. The tilt angle was 45°. The spheronized agglomerates thus formed were sized in different fractions (c. 80.315, 0.315–0.5, 0.5–071, 0.71–1 and>1 mm) by passing a gyro-vibrating sieve (Russel Finex), as known in the art. This sieving shows that the size of the agglomerates is strongly dependent on the size and form of the screws. The final hardness of the agglomerates is determined by the spheronization procedure. The results are shown in FIG. 5.

Example 4

The relationships between the size of the agglomerates and the speed of the screws and the size of the agglomerates and the size of the screws were studied as follows.

Micronised terbutaline sulphate (MMD 1.2 μm) was fed to a K-Tron twin-screw feeder with different screws and speeds. A motor setting of 30 was used for the short pitch screws, while a motor setting of 10 (⅓ as fast) was used for the long pitch screws (15 gram/min). The agglomerates were sized through 3 net dimensions (0.3, 0.5, 0.7 mm). It was found that the agglomerate size depends less on the speed of the screws than on the size of the screws, as shown in FIG. 6.

Example 5

Micronised terbutaline sulphate was agglomerated and spheronized. The resulting agglomerates were thereafter sized into different fractions and each fraction was filled into a powder inhaler. The metered dose was thereafter determined for each fraction. The results shown in FIG. 7 give about 20% difference in dose when using different agglomerate sizes. This clearly indicates the necessity of using a uniform size of the agglomerates in order to obtain a constant dose.

Other embodiments are within the claims. For example, the construction and the size of the screw feeders as well as the speed and the length of the screws could be modified. The mesh size of the sieves could also be modified. Additional screws may also be used in the same manner, arranged side-by-side in the same "nested" fashion with the two screws described above.

It is also possible to modify the size, shape, speed and tilting angle of the granulating pan or drum thereby changing the size of the final agglomerates. The spheronization could also be done in a so called "Marumerizer" apparatus for spheronization. The spheronization could also be done in any other suitable way using a rotatable rotation-symmetrical receptacle or container, e.g., any container having a cylindrical or barrel shape.

While the preferred embodiments described have involved agglomeration of particular medicaments, the method of the invention may be used to agglomerate other finely divided powders.

We claim:

1. A method of treating a finely divided powder to form a free-flowing spheronized powder, comprising the steps of:
   a) providing a substantially dry finely divided powder;
   b) feeding the substantially dry finely divided powder through a screw feeder to form agglomerates; and
   c) spheronizing the agglomerates, in substantially dry form, to form a free-flowing spheronized powder.

2. A method of claim 1 wherein the spheronization step comprises placing the agglomerates in a tilted container and rotating the container to tumble the agglomerates.

3. A method of claim 1 or 2 wherein the spheronization step is performed for about 2 to 20 minutes.

4. A method of claim 2 wherein the container is a granulating pan.

5. A method of claim 2 further wherein the container is provided with at least one scraper.

6. A method of claim 2 wherein the container is tilted at an angle of from 10°–80° from a vertical axis.

7. A method of claim 2 wherein the container is tilted at an angle of from 30°–60° from a vertical axis.

8. A method of claim 2 wherein the container is rotated at a periphery speed of from about 0.5 to 1.0 m/s.

9. A method of claim 1 further comprising the step of sizing the agglomerates by passing the agglomerates through a sieve.

10. A method of claim 1 wherein the particle size of the finely divided powder is less than 10 μm and the size of the agglomerates after the final step of the method is less than 2 mm.

11. A method of claim 1 wherein the screw feeder comprises twin concave screws.

12. A method of claim 11 wherein the screws have a pitch of from about 2 to 20 mm.

13. A method of claim 1 further comprising the step of, between step (a) and step (b), sizing the agglomerated powder to give the agglomerates a substantially uniform size.

14. A method of claim 1 or 13 further comprising the steps of, after step (b), sizing the spheronized agglomerates and repeating the spheronization step.

15. A method of claim 1 further comprising the step of metering a predetermined amount of the spheronized agglomerates into a breath actuated dry powder inhaler provided with means for deagglomerating the agglomerates during inhalation.

16. A method of claim 15 further comprising the step of actuating the inhaler, causing the spheronized agglomerates to be deagglomerated into primary particles by the means for deagglomerating.

17. A method of claim 1 further comprising the step of selecting the finely divided powder from the group consisting of terbutaline, budesonide and lactose.

18. A spheronized agglomerated powder formed by feeding a substantially dry finely divided powder through a screw feeder to form agglomerates and spheronizing the agglomerates, in substantially dry form, to form a free-flowing powder.

19. A spheronized agglomerated powder of claim 18 wherein said spheronized agglomerates have a hardness of less than 100 mN.

20. A spheronized agglomerated powder of claim 19 wherein the spheronized agglomerates have a hardness of less than 20 mN.

21. A spheronized agglomerated powder of claim 20 wherein the spheronized agglomerates have a hardness of between 0.5 and 20 mN.

22. A spheronized agglomerated powder of claim 18 wherein the particle size of the finely divided powder is less than 10 μm and the size of the agglomerates after the final step of the method is less than 2 mm.

23. A spheronized agglomerated powder of claim 18 wherein said finely divided powder is selected from the group consisting of terbutaline, budesonide and lactose.

24. A method of treating a finely divided powder comprising the steps of:
   a) feeding the powder through a screw feeder to form agglomerates;
   b) spheronizing the agglomerates; and
   c) metering a predetermined amount of the spheronized agglomerates into a breath actuated dry powder inhaler provided with means for deagglomerating the agglomerates during inhalation.

25. The method of claim 24 further comprising the step of actuating the inhaler, causing the spheronized agglomerates to be deagglomerated into primary particles by the means for deagglomerating.

26. A spheronized agglomerated powder formed by feeding a substantially dry finely divided powder through a screw feeder to form agglomerates and spheronizing the agglomerates, in substantially dry form, to form a free-flowing powder, said spheronized agglomerates having sufficient softness to allow a portion of the agglomerates to be deagglomerated into primary particles by air turbulence during inhalation by a patient through a dry powder inhaler.

* * * * *